United States Patent [19]

Magill et al.

[11] 4,439,147
[45] Mar. 27, 1984

[54] BITE-TAKING DEVICE

[76] Inventors: Thomas S. Magill, 2024 Willow Ave. N., Minneapolis, Minn. 55411; Deborah A. Keys, 2200 Grand Ave. S. #2, Minneapolis, Minn. 55405

[21] Appl. No.: 222,126

[22] Filed: Jan. 2, 1981

[51] Int. Cl.³ .............................................. A61C 7/00
[52] U.S. Cl. ...................................................... 433/3
[58] Field of Search ...................... 433/5, 3, 37, 38, 40, 433/42, 44

[56] References Cited

U.S. PATENT DOCUMENTS

| | | | |
|---|---|---|---|
| 1,076,534 | 10/1913 | Wallen | 433/44 |
| 2,683,313 | 7/1954 | Matzen | 433/3 |
| 3,107,428 | 10/1963 | Freeman | 433/43 |
| 3,411,723 | 11/1968 | Kohn | 433/141 |

Primary Examiner—Robert Peshock

[57] ABSTRACT

An elongated plastic handle having an integrally formed biting panel secured at one end with upper and lower stops, the biting panel having a thickness of at least 1 millimeter and a length in excess of the thickness of the incisor teeth, such that the biting panel can be inserted between the upper and lower incisor teeth and pulled outwardly to engage the upper and lower stops and thereby guide the teeth into an accurate construction bite for the fitting of an orthodontic appliance.

7 Claims, 5 Drawing Figures

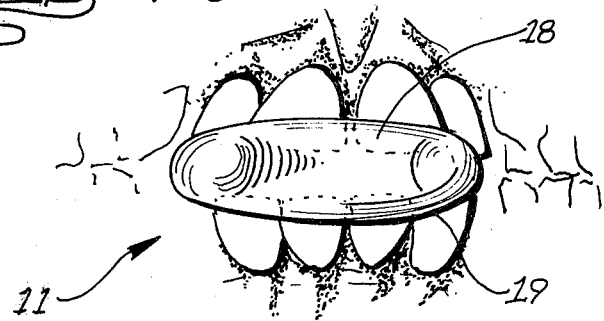
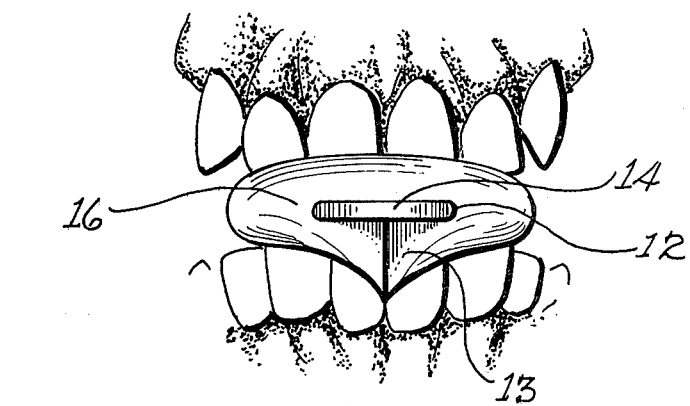

BITE-TAKING DEVICE

BACKGROUND OF THE INVENTION

This invention relates to dental tools, and, more particularly, to a device for facilitating the fabrication of functional orthodontic appliances by providing accurate alignment of the teeth preparatory to the fabrication process.

Orthopedic appliances have been increasingly used since the 1930's in both children and adults for correcting improper alignment of the teeth. Orthodontic appliances, such as those disclosed in U.S. Pat. No. 4,239,487 (Removable Orthodontic Appliances; Murdock, inventor) and which are molded to accurately conform to the teeth and jaws of the individual user, have proven to be especially valuable in correcting malocclusions such as overbite and underbite, and open bite, where the upper and lower incisors do not contact one another.

In the fabrication of orthopedic appliances for use in closed bite cases, the typical first step is to obtain what is termed a "construction bite". The construction bite corresponds to the proper alignment of the jaw and teeth with the finished orthopedic appliance in position within the patient's mouth. In order to achieve the optimum correction of the misalignment, it is required that the construction bite be obtained as accurately as possible. When an accurate construction bite has been obtained a wax mold inserted between the posterior teeth will be imprinted with such construction bite, and can thereafter be used in the fabrication, such as by molding, of the finished orthopedic appliance.

In obtaining construction bites, dentists and dental technicians have relied on visual sighting and manual manipulation of the jaws to properly align the teeth. Additionally, dentists have used tongue depressors inserted between the upper and lower incisors to achieve proper spacing therebetween, together with visual alignment of the midpoints of the upper and lower incisors. That is, with an increasing number of orthodontic appliances, the upper and lower incisors must be spaced apart to accommodate biting surfaces of the appliances themselves, thereby requiring accurate vertical, horizontal, and rotational alignment of the teeth preparatory to the construction bite. Although visual sighting of the midline of the upper and lower incisors have proven satisfactory in achieving rotational alignment, such method, whether alone or in combination with manual manipulation of the jaws, has not proven satisfactory in achieving accurate horizontal and vertical alignment.

SUMMARY OF THE INVENTION

In accordance with this invention there is provided a bite aligning device comprising a handle portion, a biting panel secured to one end of the handle portion and having a depth of at least one millimeter and a length in excess of the thickness of the incisor teeth, and upper and lower stops secured to the biting panel outwardly of the handle for abutting the upper and lower incisors. The biting panel is inserted into the patient's mouth and into contact with the upper incisors just in front of the upper stop, after which the patient is directed to gently bite down so as to bring the lower incisors against the biting panel on the undersurface thereof. As the patient gently bites onto the biting panel, the handle is drawn outwardly to bring the stops against the rear portion of the upper and lower incisors, while at the same time visually sighting the upper and lower incisors to obtain proper mid-line adjustment. Upon completion of this process the teeth will be in accurate alignment as to both horizontal and vertical alignment, in addition to mid-line or rotational alignment.

It is a primary object of this invention to provide a bite aligning device for facilitating the taking of accurate construction bites in the fabrication of functional orthopedic apliances.

It is a further object of this invention to provide a bite aligning device which can be easily used by dentists and dental technicians for vertical and horizontal alignment of the teeth during the taking of the construction bite, while at the same time allowing visual determination of the mid-line alignment.

It is another object of this invention to provide a bite-aligning device of simple construction and inexpensive materials and yet which is capable of providing accurate alignment of the teeth during a construction bite.

BRIEF DESCRIPTION OF THE DRAWINGS

FIG. 3 is a view from the interior of the patient's mouth showing the end of the bit-aligning device running across the incisors;

FIG. 4 is an inline view from the outside of the patient's mouth showing the bite-aligning device in alignment position; and FIG. 5 is a side-elevational view showing the bite-aligning device in an alternate alignment position.

DESCRIPTION OF THE PREFERRED EMBODIMENT

Figure 1:
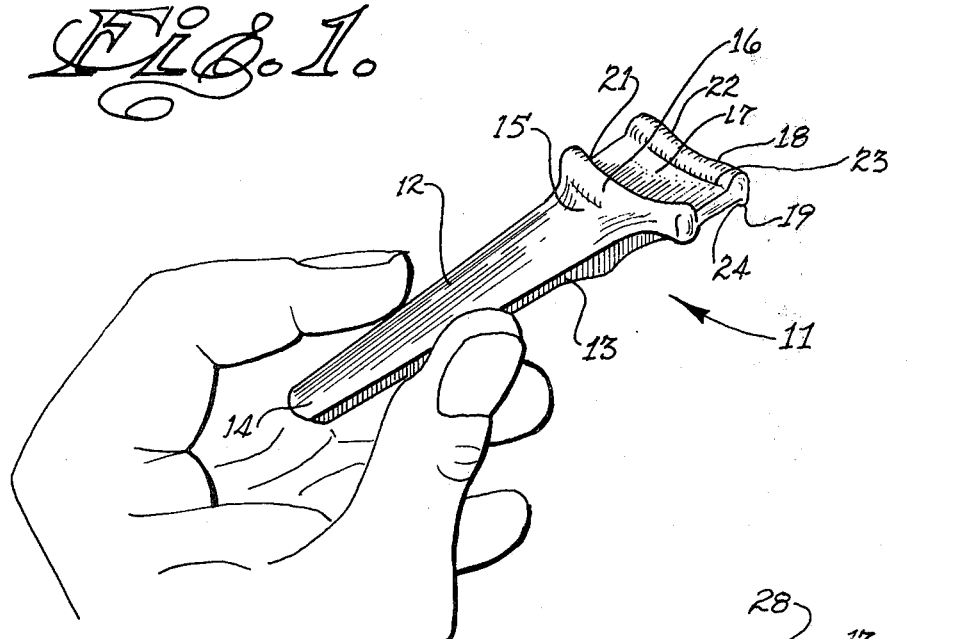
FIG. 1 is a perspective view of the bite-aligning device of this invention.

Referring to FIG. 1, bite-aligning device 11 comprises an elongated handle 12 having a ridge 13 running from its outer end 14 to its inner end 15. Integrally formed with elongated handle 12 is enlarged portion 16, biting panel 17, and stops 18, 19. Enlarged portion 16 and stops 18, 19 have curved surfaces 21, 22 corresponding to the curvatures of the incisors and generally extending the width of the incisors. Biting panel 17 extends a length in excess of the thickness of the incisor teeth, i.e., the length from enlarged portion 16 to stops 18, 19. Surfaces 23, 24 of stops 18, 19, are adapted to abut the rear portions of the upper and lower incisors, whereas in its alternate use, as shown in FIG. 5, surfaces 25, 26 or enlarged portion 16 are adapted to abut the outer surfaces of the upper and lower incisors.

Figure 2:
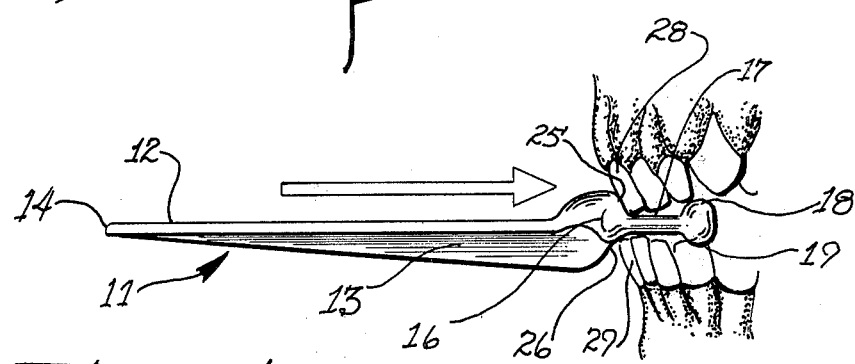
FIG. 2 is a side-elevational view showing the bite-aligning device positioned within the patient's mouth after completion of the adjustment process.
Figure 2:
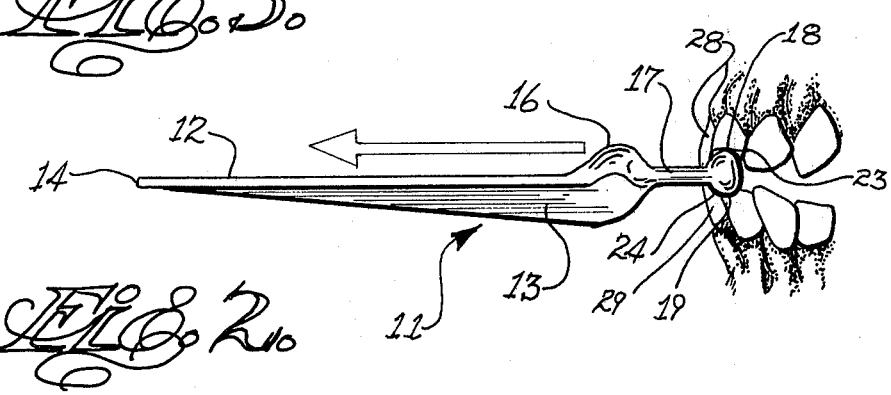

In use of the bite-aligning device of this invention, the biting panel 17 is inserted into the patient's mouth and brought upward against the upper incisors just in front of stop 18. The patient is then directed to gently bite down until the lower incisors contact the undersurface of biting panel 17, after which the handle is pulled gently outwardly to bring the upper and lower incisors into abutting relationship with stops 18, 19, while at the same time visual sighting is made of the upper and lower incisors to achieve accurate midline adjustment. Upon completion of such process the teeth will be in proper vertical, horizontal and midline adjustment, as shown in FIG. 2. As shown in FIG. 2, surfaces 23 and 24 of stops 18, 19 have been brought into abutting relationship with the inner surfaces of the upper and lower incisors 28, 29. In such position, the upper and lower teeth are in accurately spaced apart or vertical relationship for use with an orthodontic appliance having a biting portion of a depth corresponding to the depth of biting panel 17. That is, if the vertical spacing for the finished orthodontic appliance is to be one millimeter, then the bite-aligning device used will have a biting panel with a depth of one millimeter. Upon achieving the position shown in FIG. 2, the abutting relationship of stops 18, 19 will also achieve accurate horizontal alignment, leaving only the midline adjustment to be visually sighted during use of the bite-aligning device. As a result, all adjustments of the teeth and jaws can be accomplished readily and with a great deal of accuracy.

As shown in FIG. 3, stops 18, 19 extend across all four upper and lower incisors. The height of the stops 18, 19, is not critical, so long as a sufficient portion of the upper and lower incisors are contacted in order to draw the upper and lower laws into proper horizontal alignment.

As shown in FIG. 4, ridge 13 running from enlarged portion 16 of handle 12 outwardly to the end 14 thereof can be seen from the end on position when the bite-aligning device is in its alignment position. The lower peak of ridge 13 can be used in aiding the user to obtain the most accurate midline positioning of the upper and lower jaws.

In obtaining an accurate construction bite, a sheet of pink base plate wax is warmed in a water bath and rolled to approximate the coverage of the posterior teeth only. It is unnecessary to include the anterior teeth in obtaining a construction bite. The warmed wax roll is placed on the lower posterior teeth and the bite-aligning device is then inserted into the patient's mouth and used as described above. Upon the completion of the process, as shown in FIG. 2, the jaws are opened and the bite-aligning device is removed, along with the wax roll bearing the imprint of the construction bite. The wax roll bearing such construction bite is then used in conventional molding techniques to provide the finished orthodontic appliance.

Referring to FIG. 5, showing an alternate use of the bite-aligning device 11 of this invention, surfaces 25, 26 of enlarged portion 16 have been brought into abutting relationship with the outer surfaces of upper and lower incisors 28, 29. Alternate use of the bite-aligning device 11 is required where the upper and lower incisors do not extend perpendicularly from the jaw but are at an angle as shown in FIG. 5. To use stops 18, 19 in such cases would result in misalignment of the jaw. The upper surface of enlarged portion 16 is slanted from biting panel 17 toward panel 12 to further account for inward angling of the upper incisors so as to further assure accurate horizontal alignment of the jaw.

It is claimed:

1. A bite-aligning device comprising a handle, a biting panel integral to one end of the handle and having a depth of at least one millimeter and a width in excess of the distance between the upper and lower incisor teeth, a first pair of upper and lower stops secured between the handle and the biting panel, and a second pair of upper and lower stops secured opposite the first pair, the first pair of stops extending above the level of the biting panel to a height sufficient to contact only a portion of the upper and lower incisors.

2. The bite-aligning device of claim 1 wherein the upper stop of the second set of stops is slanted toward the handle from the biting panel.

3. The bite-aligning device of claim 1 wherein the biting panel and stops have a width corresponding to that of the upper and lower incisors.

4. The bite-aligning device of claim 1 wherein the biting panel and stops are curved to accommodate curvature of the incisors.

5. The bite-aligning device of claim 1 wherein the handle has a ridge running along its undersurface from the outer end thereof to the inner end thereof.

6. The bite-aligning device of claim 1 wherein the handle, biting panel and stops are integrally formed of plastic.

7. The bite-aligning device of claim 1 wherein the handle is secured perpendicularly to the biting panel.

* * * * *